United States Patent
Schneider et al.

(10) Patent No.: US 9,522,231 B2
(45) Date of Patent: Dec. 20, 2016

(54) INFUSION DEVICE WITH SAFETY FEATURE FOR PREVENTING INADVERTENT ACTIVATION

(71) Applicant: Becton, Dickinson and Company, Franklin Lakes, NJ (US)

(72) Inventors: Jared Schneider, Cranston, RI (US); Mark Guarraia, Cranston, RI (US); Margaux Boyaval, Warwick, RI (US); Ryan Shafer, Whitinsville, MA (US); Richard Cronenberg, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 83 days.

(21) Appl. No.: 14/394,020

(22) PCT Filed: Apr. 12, 2013

(86) PCT No.: PCT/US2013/036391
§ 371 (c)(1),
(2) Date: Oct. 10, 2014

(87) PCT Pub. No.: WO2013/155426
PCT Pub. Date: Oct. 17, 2013

(65) Prior Publication Data
US 2015/0080799 A1    Mar. 19, 2015

Related U.S. Application Data

(60) Provisional application No. 61/624,214, filed on Apr. 13, 2012.

(51) Int. Cl.
*A61M 5/168*   (2006.01)
*A61M 5/142*   (2006.01)
*A61M 5/20*    (2006.01)

(52) U.S. Cl.
CPC ..... *A61M 5/16831* (2013.01); *A61M 5/14248* (2013.01); *A61M 2005/14252* (2013.01);
(Continued)

(58) Field of Classification Search
CPC ........... A61M 2005/14252; A61M 2005/2073; A61M 2205/276; A61M 2205/582; A61M 2205/583; A61M 2205/584; A61M 2205/586; A61M 5/14248; A61M 5/16831
See application file for complete search history.

(56) References Cited

U.S. PATENT DOCUMENTS

| 5,858,001 A | 1/1999 | Tsals |
| 7,780,639 B2 * | 8/2010 | Van Lue ............ A61B 17/3462 604/264 |

(Continued)

FOREIGN PATENT DOCUMENTS

| CN | 2739926 Y | 11/2005 |
| CN | 101478999 A | 7/2009 |
| WO | WO-2011084951 A2 | 7/2011 |

OTHER PUBLICATIONS

Chinese Office Action dated Apr. 28, 2016 that issued in counterpart Patent Application No. 201380026302.X.

*Primary Examiner* — Bhisma Mehta
*Assistant Examiner* — Brandy S Lee
(74) *Attorney, Agent, or Firm* — Dickinson Wright PLLC

(57) ABSTRACT

A safety feature for a wearable infusion device is disclosed. The safety feature is configured to prevent accidental activation of the infusion device by protecting the activation button of the infusion device prior to and after the actuation of the activation button. The safety feature includes a wall section that protrudes from the main body of the infusion device in the vicinity of the activation button. A cover device covers the activation button prior to the actuation of the activation button. The cover device slides on the main body (Continued)

of the infusion device. When the cover covers the activation button, movement of the cover is restricted by the protruding wall section adjacent to the activation button, to hold the cover in position over the activation button.

12 Claims, 6 Drawing Sheets

(52) U.S. Cl.
CPC ............ *A61M 2005/2073* (2013.01); *A61M 2205/276* (2013.01); *A61M 2205/582* (2013.01); *A61M 2205/583* (2013.01); *A61M 2205/584* (2013.01); *A61M 2205/586* (2013.01)

(56) References Cited

U.S. PATENT DOCUMENTS

| | | |
|---|---|---|
| 2004/0025877 A1 | 2/2004 | Crowder |
| 2004/0116847 A1* | 6/2004 | Wall .................... A61K 9/0019 604/93.01 |
| 2008/0125065 A1 | 5/2008 | Das |
| 2009/0240240 A1* | 9/2009 | Hines ................ A61M 5/14248 604/890.1 |
| 2009/0326472 A1 | 12/2009 | Carter et al. |
| 2011/0112484 A1 | 5/2011 | Carter et al. |

* cited by examiner

INFUSION DEVICE WITH SAFETY FEATURE FOR PREVENTING INADVERTENT ACTIVATION

CROSS-REFERENCE TO RELATED APPLICATION

This application claims priority under 35 USC §119(e) from U.S. Provisional Patent Application Ser. No. 61/624,214, filed on Apr. 13, 2012, the disclosure of which is incorporated herein by reference in its entirety.

FIELD OF THE INVENTION

The present invention relates generally to a safety feature for an infusion device, and in particular, for a wearable infusion device such as a patch pump, wherein the safety feature prevents inadvertent activation of the infusion device.

BACKGROUND OF THE INVENTION

Devices for delivering medicament to a patient are known in the art. One type of drug delivery device is identified as a wearable infusion device or patch pump. These devices are intended for attachment to a patient's skin for self-administration of a medicament, such as insulin. Wearable infusion devices are generally intended for patients who prefer only a single needle insertion in a 2-3 day period, rather than 8-12 normal insulin injections in the same period. The advantage of wearable infusion devices is that the patient is subjected to fewer needle sticks than other delivery methods, such as a syringe or an injection pen.

When the wearable infusion device is attached to a patient's skin and activated, a hollow needle from the infusion device is injected into the patient's skin, and a drive mechanism to administer the medicament to the patient via the needle is actuated. Typically, in an infusion device, the needle is in communication with a reservoir containing the medicament. U.S. Pat. No. 5,858,001 to Tsals et al., incorporated herein by reference, discloses an infusion device which is activated by a swivel action of a main body containing a reservoir of medicament in relation to a member attached to a patient's skin. Upon activation, the device of Tsals et al. is primed and causes a needle to penetrate the skin of a patient and administer the medicament. The needle remains attached to the skin until the device is removed. Other types of infusion devices are known in the art.

In some infusion devices, activation can be awkward or imprecise, causing discomfort to the user. For instance, in the device of Tsals et al., a pivoting action of a main body containing the medicament reservoir and the needle against a member attached to the patient's skin is required, which requires additional space for activation, possible discomfort to the user, possible exposure of the needle to unwanted contact, and other related problems. Prior art infusion devices may also be prone to accidental activation since they sometimes lack safety devices that can prevent accidental activation.

Accordingly, a need exists for an improved infusion device, particularly a wearable infusion device, in which activation of the device is discrete, sanitary and accurate, and that minimizes the likelihood of unintended activation.

SUMMARY OF THE INVENTION

An object of the present invention is to provide an infusion device, particularly a wearable infusion device, that is capable of precise activation, the infusion device having a safety feature to minimize the likelihood of accidental activation, while providing optimal comfort of use and convenience to the user.

This and other objects are substantially achieved by providing an infusion device with a safety feature that is intended to prevent accidental activation of the infusion device, wherein the safety device conforms to the shape of the infusion device to minimize bulkiness and discomfort to the user.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF THE EXEMPLARY EMBODIMENTS

FIGS. 1-6 illustrate a first exemplary embodiment of the present invention.

The wearable infusion device 1 includes a main body 10 in which a reservoir (not shown) is housed. The reservoir is filled with a required amount of liquid medicament, typically insulin, sufficient to deliver insulin to the user for an extended period, e.g. 2-3 days. An adhesive liner 3 is attached to the back surface of the infusion device 1 and can adhere to the skin of a user at a location suitable for insulin therapy, such as the abdomen.

The infusion device 1 houses a hollow delivery needle (not shown) for delivering liquid medicament from the internal reservoir to the user via the needle. The infusion device 1 also includes a drive mechanism (not shown) for priming the delivery needle such that medicament flows to the needle from the reservoir, and for driving the delivery needle into the user's skin to deliver the medicament to the user. In order for the delivery of medicament to the patient to occur, the user/patient attaches the infusion device 1 to his or her skin via the adhesive liner 3 and activates a push button 15, which actuates the drive mechanism to insert the needle to the user's skin and deliver insulin to the patient.

Figure 2:
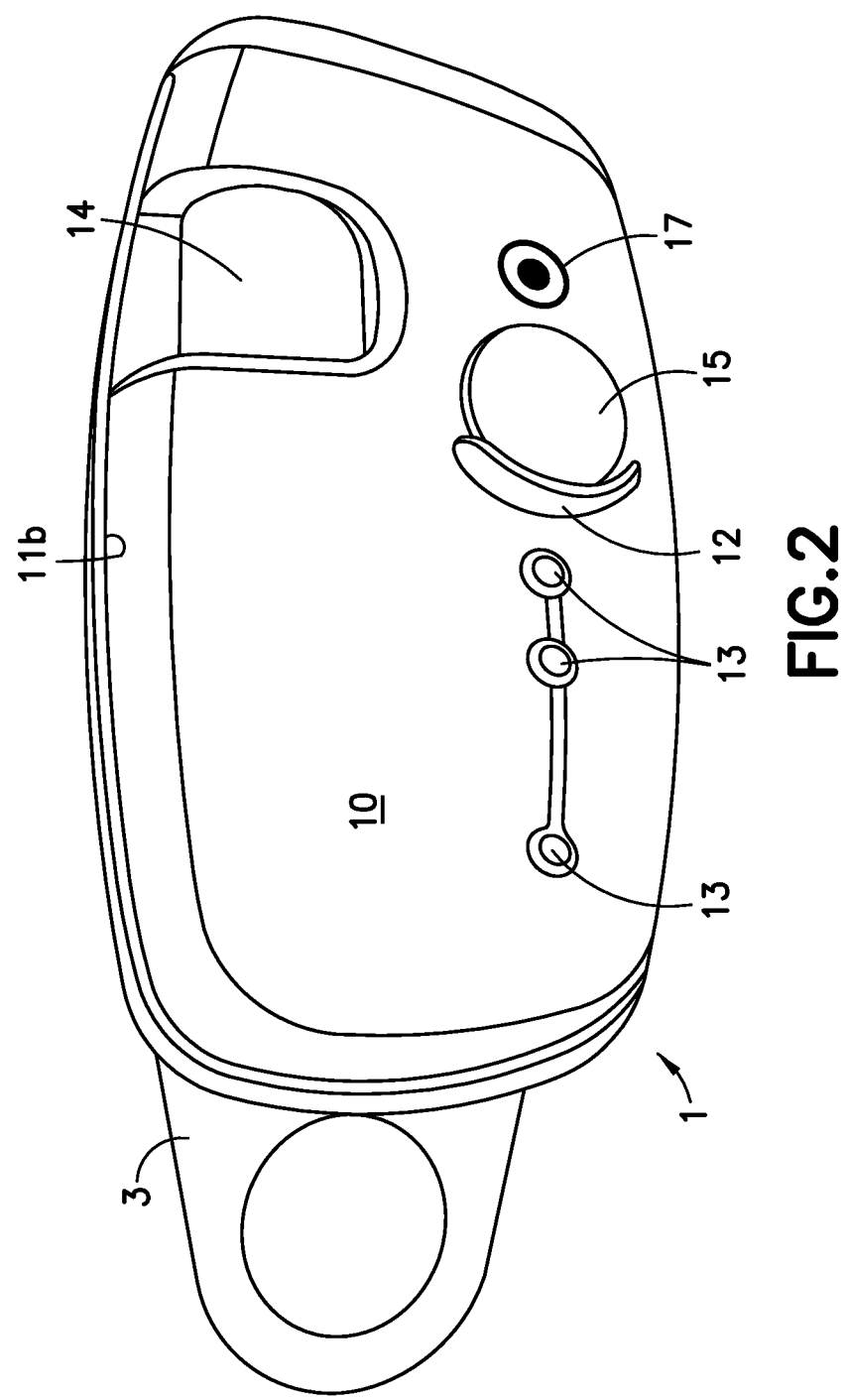
FIG. 2 is a perspective view of the infusion device of FIG. 1, illustrated without the safety cover.
Figure 3:
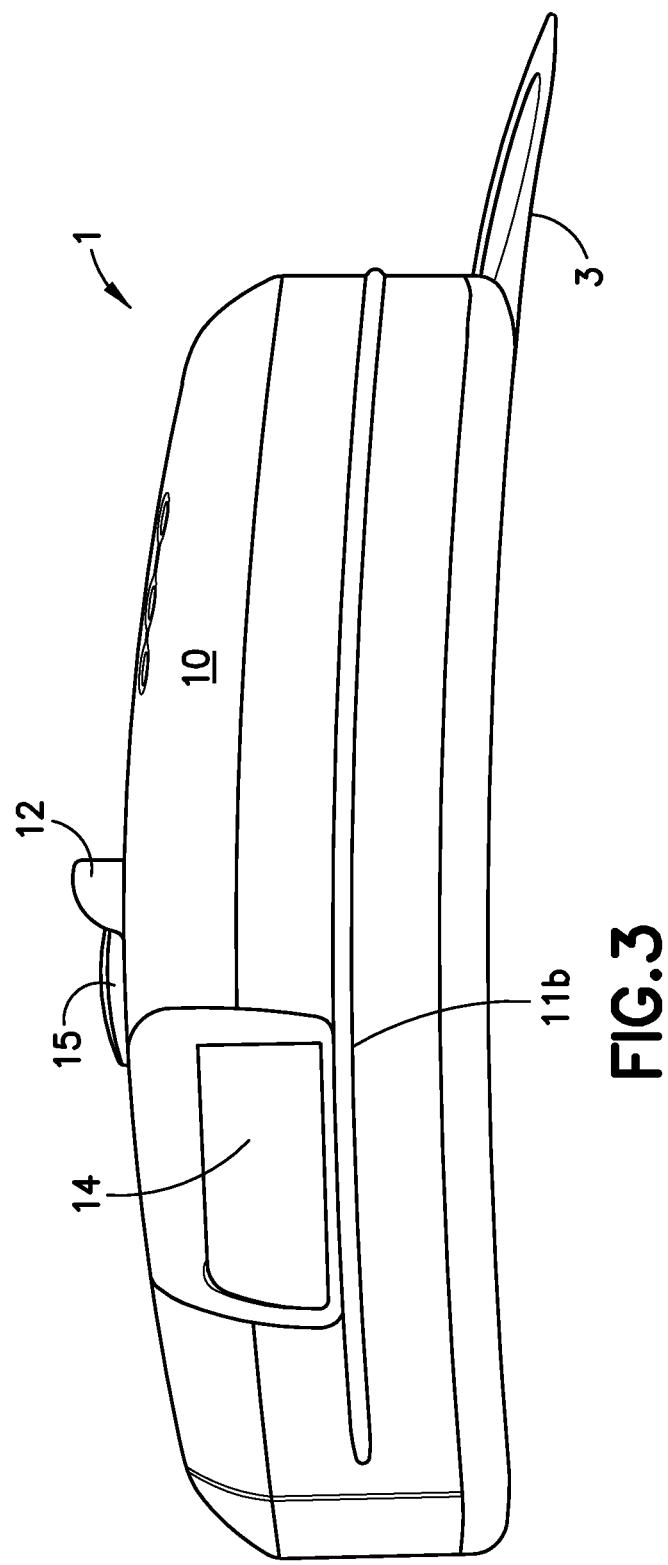
FIG. 3 is a side view of the infusion device of FIG. 2, illustrated without the safety cover.
Figure 4:
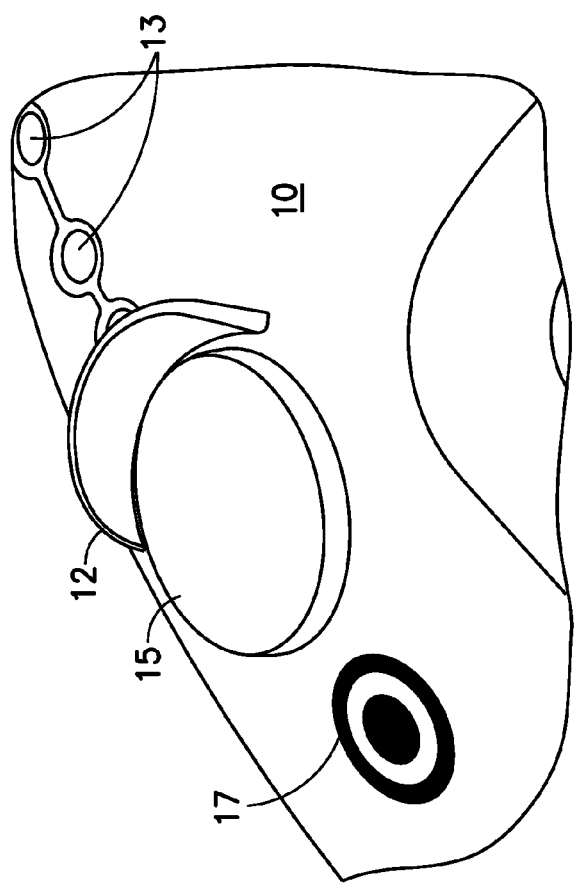
FIG. 4 is an enlarged, close-up view of the activation button and the protruding wall section of the main body of the infusion device of FIG. 2, illustrated without the safety cover.

The infusion device 1 also includes a safety feature for preventing accidental activation of the push button 15. The safety feature includes a wall portion 12 that protrudes from the main body 10 and that is preferably positioned near the push button 15, as illustrated in FIGS. 2-4. The safety feature also includes a removable safety cover 2 that is attachable to the main body 10, such that the safety cover 2 shields the push button 15 from accidental or unintended activation, as illustrated in FIG. 1.

The safety cover 2 is slidable on the main body 10 to expose the push button 15, so that the user can intentionally push the push button 10 at the appropriate time. In one embodiment, the main body 10 includes guide rails 11a, 11b on the upper and lower sides of the main body 10 (see FIGS. 1-3 and 5). The safety cover 2 includes features, such as grooves 23 on upper and lower portions thereof, that receive the guide rails 11a, 11b, such that the safety cover 2 is slidable on the main body 10 of the infusion device 1, between a first position, as in FIG. 1, wherein the safety cover 2 shields the push button 15, and a second position wherein the push button 15 does not shield the push button 15, as in FIG. 2. The safety cover 2 can remain partially attached to the main body 10 in the second position, wherein the safety cover 2 is slid away from the protruding wall portion 12 to fully expose or partially expose the push button 15 for activation. Upon activation of the push button 15, the medicament will be infused into the patent's skin until the medicament is depleted.

In another embodiment, the guide rails 11a, 11b on the main body 10 and the corresponding grooves 23 on the safety cover 2 may be replaced with magnets (not shown) for attaching and/or sliding the safety cover 2 to the main body 10. The use of magnetic forces can accurately position the safety cover 2 in relation to the push button 15. In another embodiment, the main body 10 includes one or more magnets (not shown) and the safety cover 2 includes corresponding metallic or magnetic structures (not shown), such that the safety cover 2 is attachable to the main body 10. In yet another embodiment, the safety cover 2 includes one or more magnets (not shown) and the main body 10 includes corresponding metallic or magnetic structures (not shown), such that the safety cover 2 is attachable to and slidable on the main body 10. As illustrated in FIG. 1, the safety cover 2 may include grip portions 25 that may be protrusions or indentations at upper and lower portions thereof that can assist a user to grip the safety cover 2.

Figure 1:
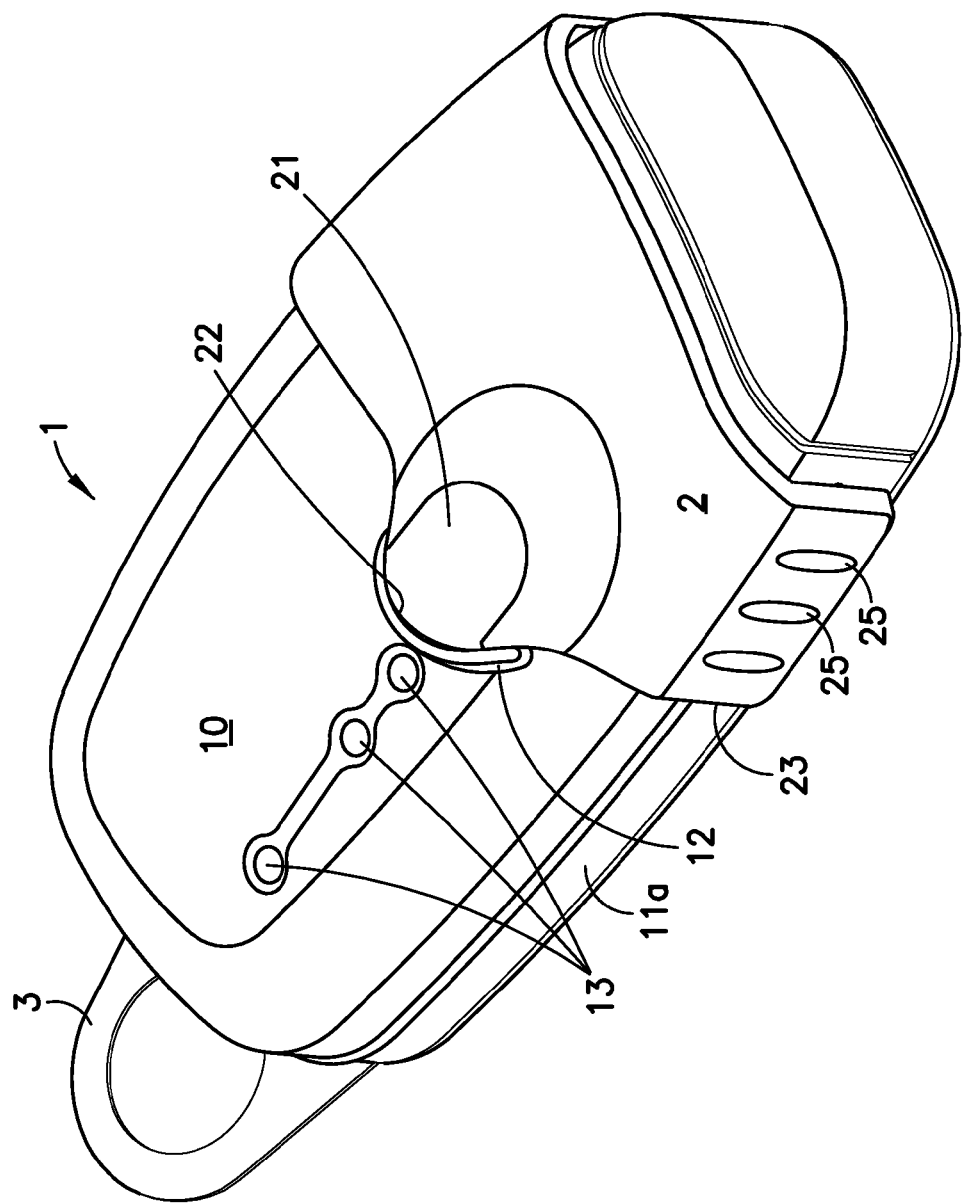
FIG. 1 is a perspective view of a wearable infusion device in accordance with an embodiment of the present invention, shown with a safety cover attached thereon.
Figure 6:
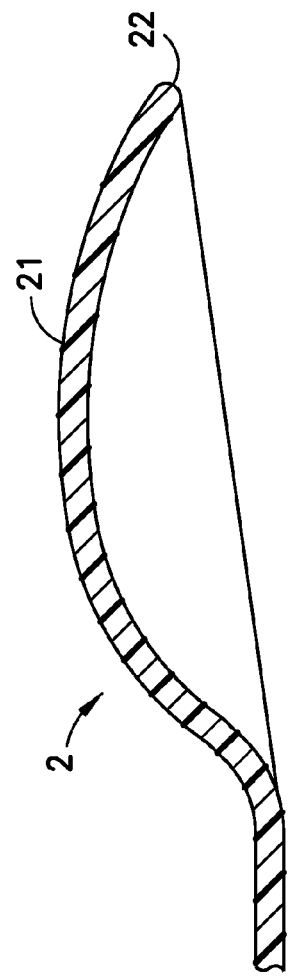
FIG. 6 is a partial cross-sectional view of the safety cover of the infusion device of FIG. 1.

In one embodiment, as illustrated in FIG. 1, the safety cover 2 includes a bulbous portion 21 for shielding the push button 15 when the safety cover 2 is at its first position. A cross-section of the bulbous portion 21 of the push button 15 is illustrated in FIG. 6. The bulbous portion 21 resembles a spoon shape and when it is positioned or slid over the push button 15, there is sufficient clearance between the bulbous portion 21 and the push button 15 such that in the event that an external force is applied to the bulbous portion 21, the push button 15 will not be unintentionally pushed or actuated.

To assist in maintaining the safety cover 2 at the first position, in which the safety cover 3 shields the push button, as illustrated in FIG. 1, the main body 10 of the infusion device 1 is provided with a protruding wall portion 12. In the first position, as illustrated in FIG. 1, the protruding wall portion 12 prevents further sliding movement of the safety cover 2 in the direction toward the protruding wall portion 12 and positions the safety cover 2 to shield the push button 15. In this position, the leading portion 22 of the bulbous portion 21 may contact the protruding wall portion 12 of the infusion device 1.

The protruding wall portion 12 is preferably configured around a periphery of the push button 15. For instance, the wall portion 12 can be a half-moon shape that recedes at its ends, as illustrated in FIGS. 3 and 4. The outer edges of the wall portion 12 are preferably rounded for user comfort.

With the cover 2 removed, as illustrated in FIG. 2, the wall portion 12 also functions to partially shield the push button 15 from being activated unintentionally, as illustrated in FIGS. 3 and 4. The wall portion 12 can also be used as a guide for locating the push button 15 for activation of the infusion device 1. This feature may be useful for discrete activation of the infusion device 1 or as a guide for the visually impaired to easily locate the push button 15.

Figure 5:
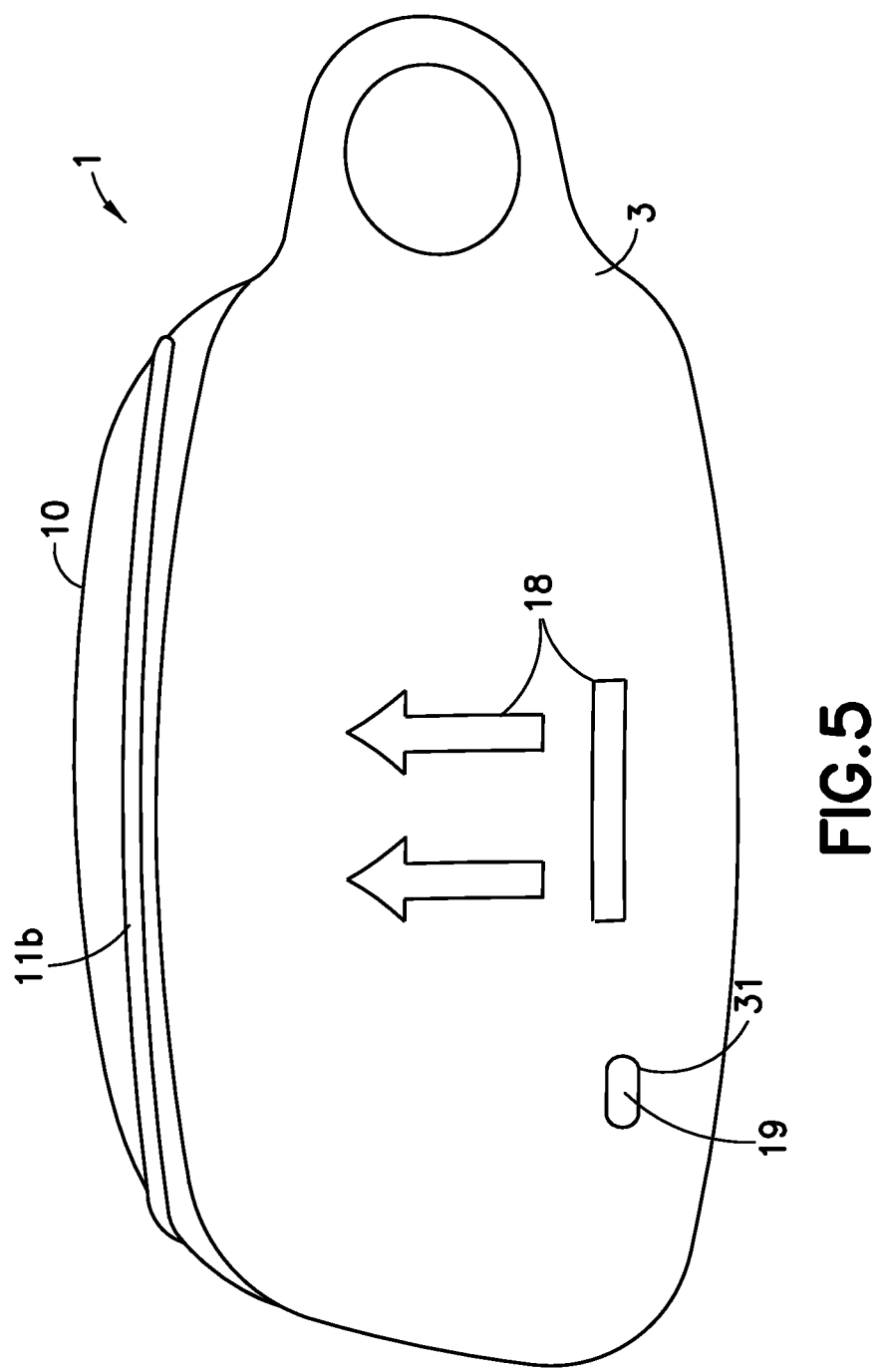
FIG. 5 is a perspective rear view of the infusion device of FIG. 2.

When the push button 15 is actuated, the delivery needle (not shown) extends from a back surface of the main body 10 of the infusion device 1. As illustrated in FIG. 5, the needle extends from an aperture 19 of the main body 10, through a slot 31 in the liner 3, to pierce the user's skin. In one embodiment, the front of the main body 10 includes one or more indicators 13, as illustrated in FIGS. 1 and 2, which indicate the various stages of infusion therapy. The indicators can be color-coded. In addition, the front of the main body 10 may include a window 14 that allows a user to see how much of the medicament remains in the reservoir and/or to monitor the operation of the infusion device 1. In one embodiment, front indicia 17 on the front of the main body 10 provides an approximate location of the needle aperture 19 on the back of the main body 10, where the needle will insert into the user's skin, as illustrated in FIG. 2. This may assist the user in inserting the needle at the desired location on the user's skin. The front indicia 17 illustrated in FIG. 2 is shown as a target (e.g., a bull's eye) mark having a solid circle surrounded by an outer circle. The front indicia 16 can be in the form of other markings, such as a cross-hair marking. The back surface of the main body 10 may include rear indicia 18 to indicate the upright position of the infusion device 1, as illustrated in FIG. 5. These rear indicia 18 are visible through a clear or see-through liner 3.

Figure 7:
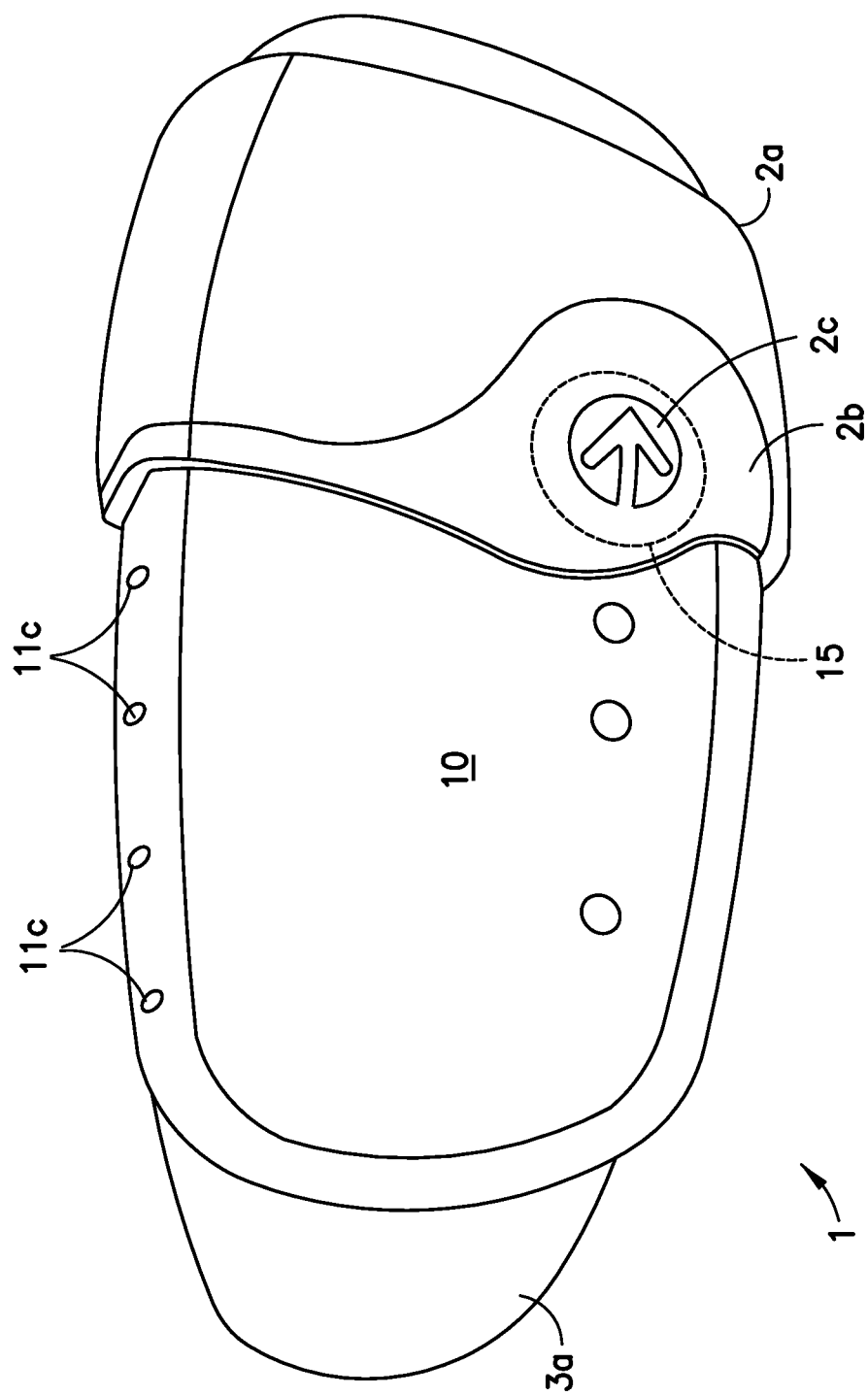
FIG. 7 is a perspective view of another wearable infusion device in accordance with an embodiment of the present invention, shown with a safety cover attached thereon.

FIG. 7 illustrates another embodiment of a wearable infusion device in accordance with the present invention. In this embodiment, the safety cover 2a includes a clear or translucent portion 2b composed of a clear or translucent material that enables the safety button 15 to be visible when the safety cover 2a is attached to the main body 10 to protect the safety button 15 from unintended activation. The clear or translucent portion 2b can include indicia 2c in the form of an arrow pointing in the direction in which the cover 2a is to be slid or removed from the main body 10 to expose the safety button 15 prior to activation thereof. The main body 10 also includes bumps 11c on its upper and lower sides, in lieu of the guide rails 11a and 11b in the embodiment of FIGS. 1-6, onto which corresponding slots (not shown) in the safety cover 2a can frictionally engage in order to attach the safety cover 2a to the main body 10. To disengage the safety cover 2a from the main body 10, the user can hold the main body 10 and push the cover in the direction of the arrow indicia 2c on the safety cover 2a, disengaging the safety cover 2a from the bumps 11c on the main body 10. FIG. 7 also shows a portion of the adhesive liner 3a, which differs from that of the adhesive liner 3 in FIG. 1 in that the former includes a circular hole while the latter does not.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

The invention claimed is:

1. An infusion device having a safety feature for preventing accidental activation, comprising:
   a main body for attachment to a user's skin;
   a reservoir housed in the main body, the reservoir comprising liquid medicament;
   a delivery needle for delivering the medicament to the skin of the user, the delivery needle housed in the main body;
   an activation button for actuating a drive mechanism;
   a wall portion protruding from the main body near the activation button; and
   a cover attachable to the main body to protect the activation button from accidental activation at a first cover position, the cover exposing the activation button to enable activation by the user at a second cover position; wherein the cover further comprises a portion for shielding the activation button when the cover is at the first cover position, such that there is sufficient clearance between the shielding portion and the activation button to prevent accidental activation of the activation button if the shielding portion of the cover is pressed; and wherein, when the cover is at the first cover position, a leading portion of the shielding portion of the cover is in contact with an outer edge of the protruding wall portion, preventing the cover from sliding over the protruding wall portion.

2. The infusion device as claimed in claim 1, wherein the shielding portion of the cover further comprises a bulbous portion for shielding the activation button when the cover is at its first position, such that there is sufficient clearance between the bulbous portion and the activation button to prevent accidental activation of the activation button if the bulbous portion of the cover is pressed.

3. The infusion device as claimed in claim 2, wherein when the cover is at its first position, the bulbous portion of the cover is in contact with the protruding wall portion, preventing the cover from sliding over the protruding wall portion.

4. The infusion device as claimed in claim 3, wherein a protrusion of the wall portion from the main body partially shields the activation button.

5. The infusion device as claimed in claim 4, wherein the wall portion is formed along a periphery of the activation button.

6. The infusion device as claimed in claim 5, wherein the wall portion comprises edges that are rounded.

7. The infusion device as claimed in claim 1, wherein the main body comprises one or more rail-type protrusions and the cover comprises one or more corresponding grooves, such that the cover is attachable to and slidable on the main body.

8. The infusion device as claimed in claim 7, wherein the cover is slidable on the main body along the respective rail-type protrusions and grooves.

9. The infusion device as claimed in claim 7, wherein the cover is slidable on the main body along the respective magnets and corresponding metallic or magnetic structures main body.

10. The infusion device as claimed in claim 1, wherein the main body comprises one or more magnets and the cover comprises corresponding metallic or magnetic structures, such that the cover is attachable to the main body.

11. The infusion device as claimed in claim 1, wherein the cover comprises one or more magnets and the main body comprises corresponding metallic or magnetic structures, such that the cover is attachable to and slidable on the main body.

12. The infusion device as claimed in claim 1, wherein the wall portion and activation button are disposed on a side of the main body that is opposite the side of the main body that is attached to the user's skin.

* * * * *